(12) United States Patent
Shenkal

(10) Patent No.: US 9,402,422 B2
(45) Date of Patent: Aug. 2, 2016

(54) HYBRID E-CIGARETTE/VAPORIZER WITH EXHALE FILTER CAPABILITY

(71) Applicant: Yuval Shenkal, Cardiff, CA (US)

(72) Inventor: Yuval Shenkal, Cardiff, CA (US)

( * ) Notice: Subject to any disclaimer, the term of this patent is extended or adjusted under 35 U.S.C. 154(b) by 0 days.

(21) Appl. No.: 14/121,917

(22) Filed: Nov. 3, 2014

(65) Prior Publication Data

US 2015/0150305 A1 Jun. 4, 2015

Related U.S. Application Data

(60) Provisional application No. 61/899,070, filed on Nov. 1, 2013.

(51) Int. Cl.
- *A24F 47/00* (2006.01)
- *A61M 15/06* (2006.01)
- *H05B 3/40* (2006.01)

(52) U.S. Cl.
CPC ............... *A24F 47/008* (2013.01); *A61M 15/06* (2013.01); *H05B 3/40* (2013.01)

(58) Field of Classification Search
CPC ...... A61M 15/06; A24F 47/00; A24F 47/002; A24F 47/008
See application file for complete search history.

(56) References Cited

U.S. PATENT DOCUMENTS

| | | | | |
|---|---|---|---|---|
| 4,899,766 A | * | 2/1990 | Ross, Jr. | A24F 47/00 131/175 |
| 5,396,907 A | * | 3/1995 | Rojas Henao | A24F 13/00 131/175 |
| 2008/0230052 A1 | * | 9/2008 | Montaser | A61M 15/0085 128/200.16 |
| 2011/0277757 A1 | * | 11/2011 | Terry | A24F 47/008 128/202.21 |
| 2014/0123990 A1 | * | 5/2014 | Timmermans | A24F 47/008 131/328 |

* cited by examiner

*Primary Examiner* — Anthony Calandra
(74) *Attorney, Agent, or Firm* — Timothy W. Fitzwilliam

(57) ABSTRACT

An electronic cigarette adaptable to vaporize liquid or flower material further with exhale filter capability is disclosed herein. In a preferred embodiment, threads are provided to disassemble a flower and/or liquid cartridge so that they can be exchanged for either/or. The flower cartridge has a separate heat transfer element not desired in the liquid cartridge. An innovative diverter valve assembly also has threads to connect to the cartridges and provides an exhale filter function so that exhaled vapor will not be offensive to non-smokers in an enclosed environment. The electronic smoking device herein further has a mini/micro USB charging port on a side thereof for its rechargeable batteries. Also in a preferred embodiment, a mouthpiece is made of relatively soft elastomer material and is flavored for comfort and enjoyment of a user.

13 Claims, 9 Drawing Sheets

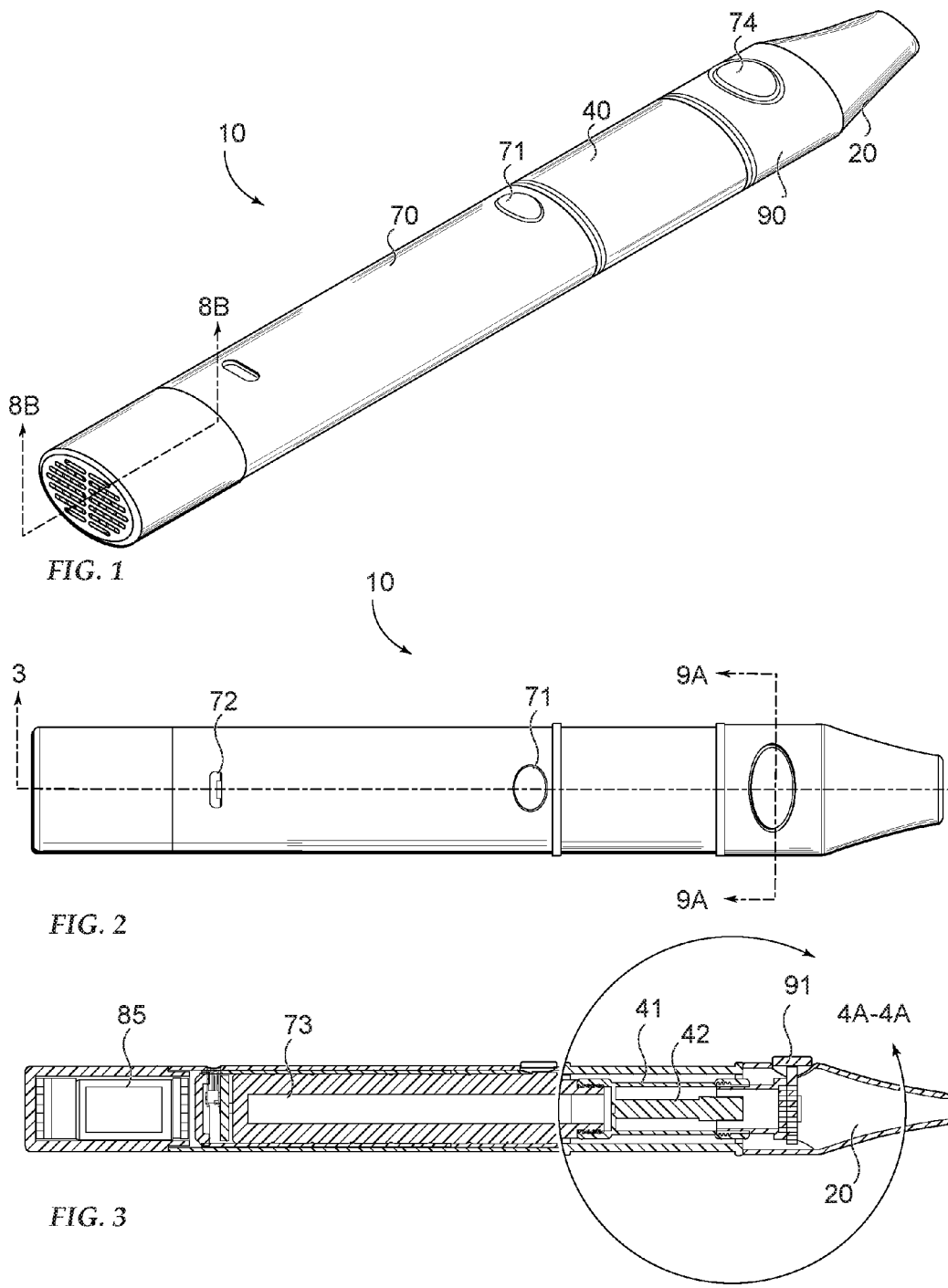

HYBRID E-CIGARETTE/VAPORIZER WITH EXHALE FILTER CAPABILITY

PRIORITY CLAIM

This patent application claims benefit of the priority date of U.S. Prov. Pat. App. Ser. No. 61/899,070 filed on Nov. 1, 2013, entitled 2n 1 Electronic Cigarette, accordingly, the entire contents of this patent application is hereby expressly incorporated by reference.

BACKGROUND OF THE INVENTION

1. Field of the Invention

The present invention pertains generally to electronic smoking devices. More specifically, the present invention relates to an electronic cigarette capable of vaporizing liquid, powder, or flower material that further has an exhale function to filter exhaled vapor.

2. Description of the Prior Art

Smoking tobacco or other plant material has notoriously been practiced in numerous cultures for many centuries. Devices for filtering exhaled smoke have also been introduced heretofore. One such early example was proposed by Martin, U.S. Pat. No. 5,353,814, entitled "Cigarette Smoke Cleansing and Smoking Device" and was awarded patent protection in 1994. Martin describes a smoking device where a traditional cigarette is smoked through a mouthpiece wherein the same mouthpiece is utilized to exhale therethrough for filtering exhaled smoke.

Importantly, in the last decade or so, traditional smoking of tobacco has been banned in places such as bars, casinos and beaches where smoking has traditionally been permitted. Smoking has additionally been banned on airline travel for at least about twenty years where no alternative has been adopted or provided. One drawback to the Martin device is that it will not completely eliminate smoke emitting from the device and any small smoke emission will be noticeable to people sensitive thereto, especially in an airline flight environment or similar enclosed space or building that's not well ventilated.

Also known heretofore are so called "electronic cigarettes" that typically use an electrical heating element to heat a liquid usually containing a mixture of nicotine and flavorings that produces a mist similar to smoke. Most electronic cigarettes however do not have complicated electronic and simply contain a battery electrically coupled to a heating element. A useful early example was proposed by Counts et al. U.S. Pat. No. 5,666,978 entitled "Electrical Smoking System for Delivering Flavors and Methods of Making Same and was awarded patent protection in 1997. This particular prior art device has a receptacle for receiving tobacco or "tobacco flavored material" and electrical heating elements configured to the device for heating the material in order to emit vapors or aerosol for delivery to a smoker.

While these prior art devices are suitable in their idiosyncratic purposes, a need remains for an alternative to smoking cigarettes that further has exhale filter capability so that same is acceptable to somewhat sensitive environments such as airlines and enclosed places where children may be present.

In light of the above, it is an object of the present invention to provide a Hybrid E-Cigarette/Vaporizer with Exhale Filter Capability that is a more versatile design the can additional provide a smoking alternative in environments that have strict bans on smoking. More specifically, it is an object of the present invention to provide an inhale function and an exhale function. It is additionally an object of the present invention to provide a design comfortable to a user. Still further, it is further an object of the present invention to provide a device that can be disassembled so that different types of cartridges can be employed. It is still further an object of the present invention to provide a design that includes a variety of innovative features over prior designs.

BRIEF SUMMARY OF THE INVENTION

The present invention specifically addresses and alleviates the above mentioned deficiencies, more specifically, the present invention, in a first aspect, is an electronic/electric cigarette and/or vaporizer comprising: an elastomer mouth piece configured to a cooker chamber containing heated material to be vaporized such as liquid, oil, flower or leaf material; and a body portion coupled to the cooker chamber wherein an electric heating element is provided to heat the heated material. The invention is additionally characterized wherein a battery is configured inside the body portion providing current to the electric heating element; and a diverter valve assembly is provided for blocking air flow through the cooker chamber and thereby allow exhaled air forced into the mouth piece to be diverted around the cooker chamber.

The electronic cigarette herein is additionally characterized in that the diverter valve assembly further comprises a diverter valve having a button for depressing with a finger or a thumb at one end; and a fixed disk configured as an abutment to the diverter valve, the fixed disk and the diverter valve each having a plurality of apertures wherein said plurality of apertures are aligned when the diverter valve is in the open position and wherein the plurality of apertures are askew when the diverter valve is in the closed position.

The invention in this aspect is additionally characterized wherein the diverter valve further comprises a pair of curved arms at an opposite end with respect to the button wherein the pair of arms are configured to deform slightly when the button is depressed and when the diverter valve is in the closed position and wherein when the button is released the arms return to an undeformed state.

The electronic cigarette of the present invention in this aspect is further characterized as comprising: a printed circuit board (PCB) coupled to the battery, the battery being a rechargeable battery; a charging circuit configured to the PCB; and a micro universal serial bus (USB) port for connecting to a power source for recharging the battery. The PCB also has a cover configured adjacent to the PCB for protecting same. Also, a micro (or mini) USB port is further accessible through an aperture in a side wall (not the end wall) in the body portion.

A filter assembly is further coupled to the body portion at a distal end thereof; and the filter assembly further comprises a corrugated paper filter and a pair of felt filters configured on opposite sides of the corrugated paper filter. In a preferred embodiment the body portion has an outer wall comprising aluminum and the cooker chamber has an outer wall comprising glass. The mouth piece comprises flavored elastomer material for the enjoyment and comfort of a user. An igniter with an igniter button is electrically configured to the battery and the heating element.

The invention in this aspect is additionally characterized in that the cooker chamber further comprises a removable liquid cartridge, and the removable liquid cartridge also has a cylindrical liquid chamber therewithin for containing the liquid to be heated by the heating element.

In a second aspect the invention is a vapor smoking device comprising: a mouth piece configured to a cooker chamber containing material to be heated; a body device coupled to a the cooker chamber wherein an electric heating element is provided to heat said heated material; a battery configured inside the body portion providing current to the electric heating element; and a filter assembly coupled to the body portion at a distal end thereof.

The invention in this aspect if further characterized in that the filter assembly further comprises: a fibrous corrugated paper filter; and a pair of felt filters configured on opposite sides of the corrugated paper filter, however with a charcoal granules filter also sandwiched therebetween. Also, the filter assembly includes a first and a second screen filter, the first screen filter adjacent to the first of the pair of felt filters, the second screen filter adjacent to a second of the pair of felt filters.

Also, the vapor smoking device includes an igniter electrically configured to the battery and the heating element; and a removable liquid cartridge configured within the cooker chamber, the igniter having threads at an end thereof, the removable liquid cartridge further having complementary threads to connect to the igniter.

In a third aspect, the invention is characterized as a vapor smoking device system comprising: a cooker chamber; a mouth piece configured to a cooker chamber containing heated material; a body portion coupled to a the cooker chamber wherein an electric heating element is provided to heat said heated material; a removable liquid cartridge configured within the cooker chamber for vaporizing liquid material; a removable flower cartridge configured within the cooker chamber, interchangeable with said removable liquid cartridge, for vaporizing flower material; and a battery configured inside the body portion providing current to the electric heating element.

The vapor smoking device system herein further comprises a diverter valve assembly for blocking air flow through the cooker chamber and thereby allowing exhaled air forced into the mouth piece to be diverted around the cooker chamber and around the batteries. The removable flower cartridge herein is additionally characterized as comprising: a mesh container for holding the flower (or leaf) material; a wire coil to transfer heat from the heating element to the mesh container, the wire coil for the purposes of dissipating heat generated by the heating element to a temperature optimum for the flower material; and an air intake port on a side wall of the flower cartridge for introducing air in the smoking device inhale function.

While the apparatus and method has or will be described for the sake of grammatical fluidity with functional explanations, it is to be expressly understood that the claims, unless expressly formulated under 35 USC §112, or similar applicable law, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC §112 are to be accorded full statutory equivalents under 35 USC §112, or similar applicable law. The invention can be better visualized by turning now to the following drawings wherein like elements are referenced by like numerals.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is an isometric view of a preferred hybrid electronic cigarette/vaporizer with exhale filter capability of the present invention;

FIG. 2 is a top plan view of the FIG. 1 embodiment;

FIG. 3 is a cross-sectional view of the invention taken along line 3-3 in FIG. 2;

DETAILED DESCRIPTION OF THE PREFERRED EMBODIMENTS

Figure 4A:
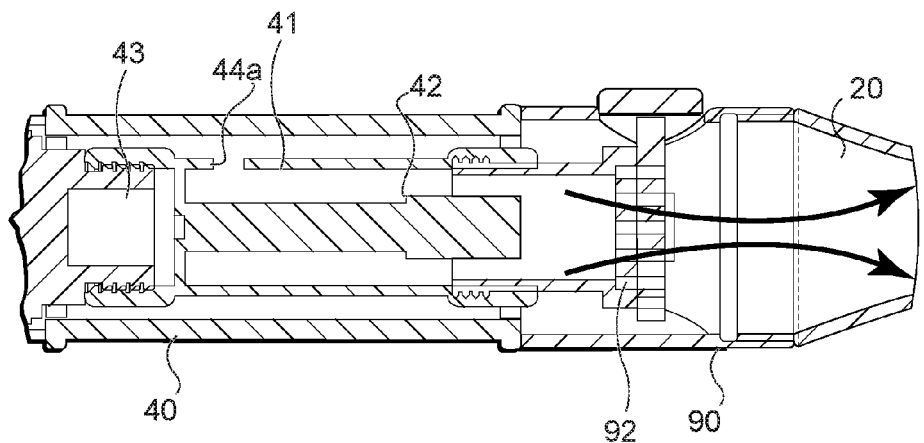
FIG. 4A is an enlarged view of the cross-section of FIG. 3 defined by the area 4A-4A.

Referring initially to FIG. 1, a first preferred embodiment 10 is illustrated in an isometric view and is generally cigar shaped. A mouth piece 20 is provided and is easily replaceable as it snugly mates with a diverter valve assembly 90. The mouth piece 20 is also unique in that it is flavored with mint, vanilla or other as may be pleasing to a user. Further, the mouth piece 20 is flexible comprising thermoplastic material providing enhance feel and comfort.

Additionally with regard to FIG. 1, a cooker chamber 40 has a glass housing and can be configured for oil/liquid material or flower/leaf material as further detailed herein. A battery compartment 70 has a housing (e.g. aluminum) configured to the cooker chamber 40 and contains apertures for the ignition 71 button and a micro (mini) USB (universal serial bus) charging port 72 additionally detailed in FIG. 2, FIG. 7E and FIG. 7F. Also with regard to FIG. 2, a top plan view of the invention 10 is provided with sectional lines drawn for revealing internal components. The cooker compartment housing 40 (e.g. glass), the battery compartment 70 and a filter assembly 80 together define a body portion 40, 70, 80 of the electric/electronic cigarette. Incidentally, the electric cigarette 10 may be defined broadly as to be a smoking device that uses a heating element to heat material and inhale vapors therefrom;

or in a preferred embodiment the e-cigarette has a printed circuit board (PCB) 74 (FIG. 7F) having circuitry, namely, a charging circuit.

Figure 4B:
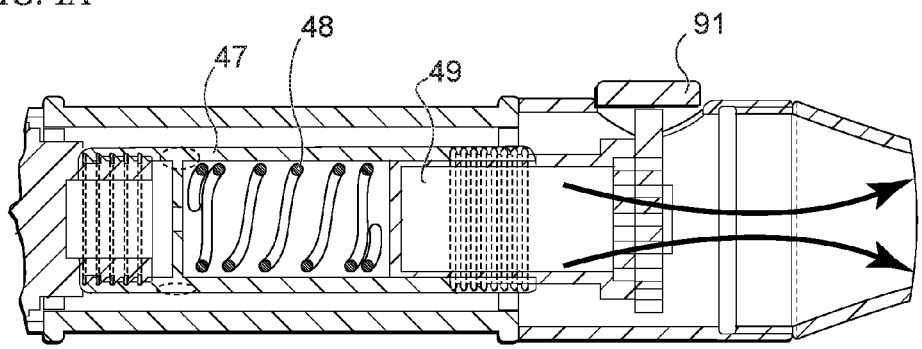
FIG. 4B is an enlarged sectional view similar to that of FIG. 4A however with the accessory piece for vaporizing leaf material.
Figure 4C:
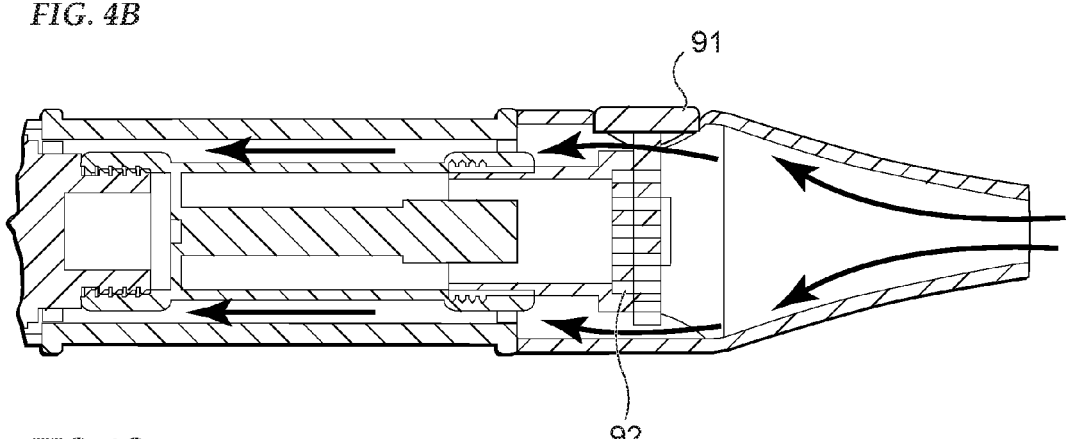
FIG. 4C is yet another similar enlarged sectional view to that of FIG. 4A however with the diverter valve pressed showing exhaled air flow through the mouth piece and cooker chamber.

Regarding FIG. 3, a cross sectional view is provided focusing attention to the cooker chamber 40 and diverter valve 91 assembly 90 used to divert air flow depending on an inhale or an exhale function of the present invention 10. FIG. 4A provides an enlarged view of this area with directional arrows showing air flow through the diverter valve in the natural unpressed state. In its operation, liquid material inside cylinder 41 is heated by an electrical heating element causing said liquid to emit a vapor for smoking FIG. 4B illustrates the versatility of the invention in that components for smoking leaf or flower material can replace the liquid cylinder and having similar air flow. With reference to FIG. 4C, the diverter valve 91 is shown being pressed blocking air flow inside the cooker cartridge 41 and instead allowing air flow around an outer channel provided between said cooker cartridge 41 and the cooker chamber 40 housing. Intake air holes 44a, 44b are provided to the cartridges 41, 46 and not to the cooker chamber 40 so that exhaled air will not expel out of any such holes.

Figure 5:
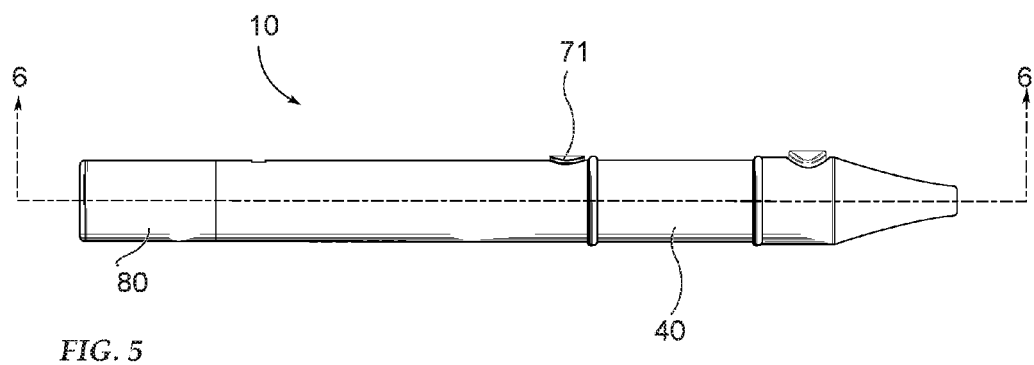
FIG. 5 is a side aspect view of the electronic cigarette.

FIG. 5 herein shows a profile view of the present invention. It should be appreciated that the cigar shaped device 10 is wider than its height in the profile view comparing FIG. 2 to FIG. 5. In other words, its end view (FIG. 8C) and cross-section (FIG. 9B) are elliptical or oval in shape allowing for more area for exhaled air flow around sides of the device.

Figure 6:
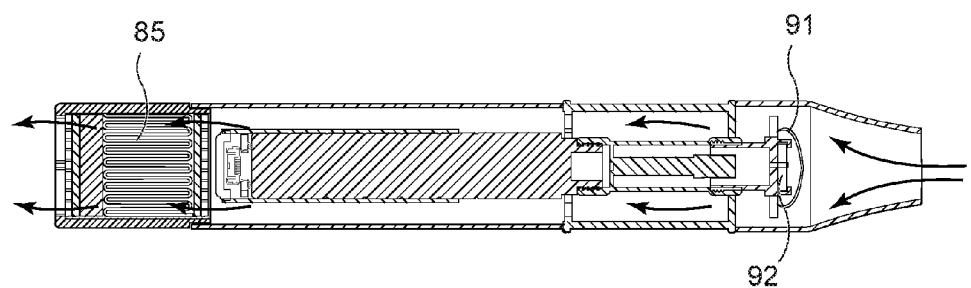
FIG. 6 is a sectional view taken along line 6-6 in FIG. 5 importantly showing exhaled air flow around an outer cylindrical channel around internal components.

FIG. 6 particularly illustrates how air flows around an outer periphery of the device. Specifically around an outer portion of the cooker chamber and the battery compartment to the end filter. In an alternative embodiment, the filter is hollow and cylindrical instead of not hollow and cylindrical 80 as shown and therefore could be configured around the battery compartment 70.

Figures 7A, 7B:
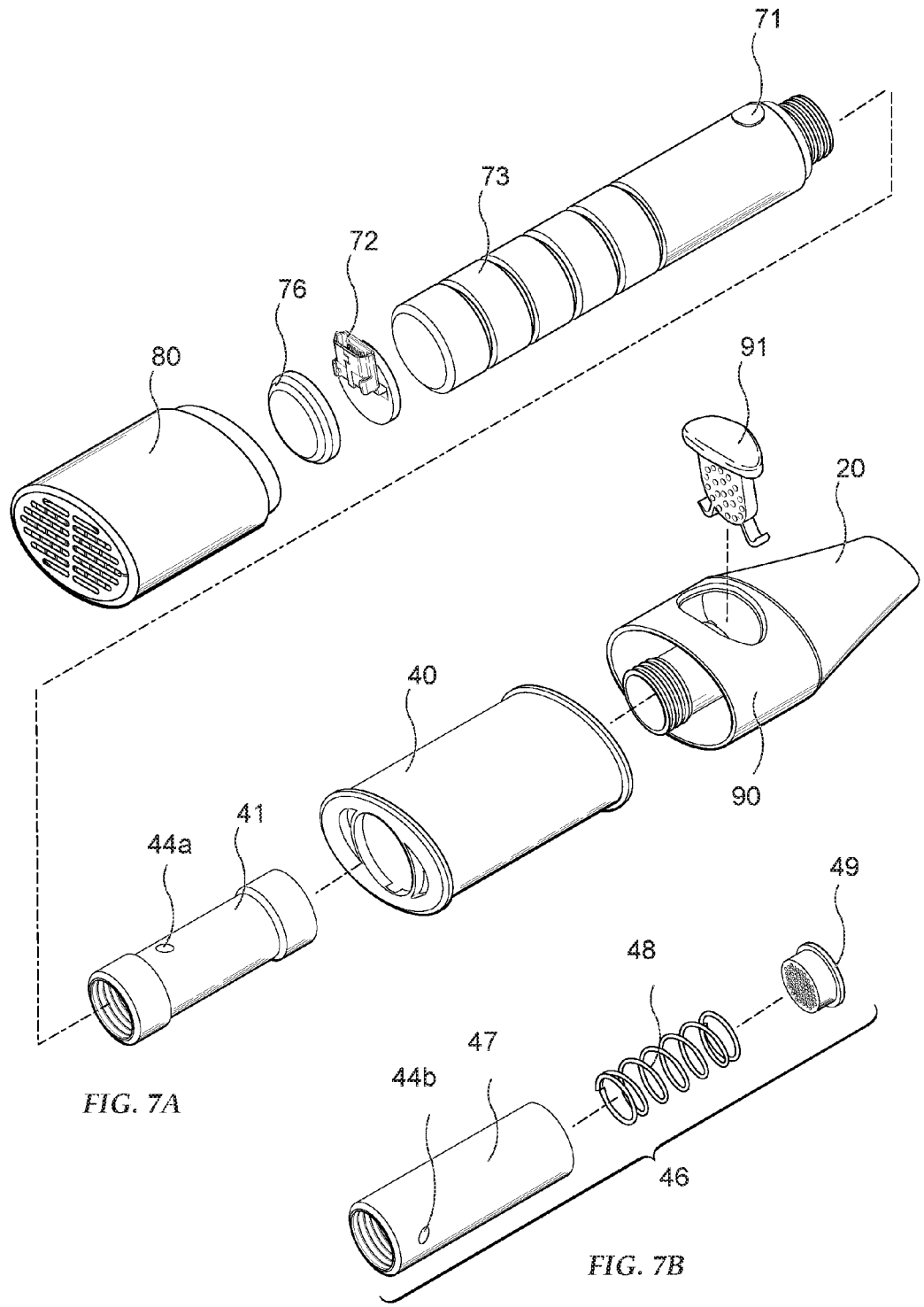
FIG. 7A is an exploded view of internal and external components of the present invention.
FIG. 7B is an exploded view of an accessory for vaporizing leaf material (flower cartridge) instead of liquid material.

With regard to FIG. 7A, is an exploded view of major components 20, 40, 70, 80, 90 of the present invention is shown. Importantly as stated, cooker chamber 40 can support two different kinds of cooker cartridges 41, 46 depending on user preference. The liquid cartridge 41 has a cylindrical liquid chamber 42 therein that can be seen in FIG. 4A for containing material to be heated. Also of note, heating element 43 is configured closer to the actual material for the liquid embodiment 41; and the alternative leaf embodiment 46 (flower cartridge) has additional components 47, 48, 49 for heating leaf material as detailed herein. Additionally notable regarding FIG. 4A, liquid cartridge 41 screws onto threads surrounding the heating element 43; and the diverter valve assembly has complementary threads to screw around an upper end of the liquid cartridge 41.

Further with regard to FIG. 7A, an igniter 71 is configured to the heating element having threads around an upper end thereof. Batteries 73 are electrically and physically coupled to the igniter 71 (FIG. 4A) and heating element 43.

Figure 7C:
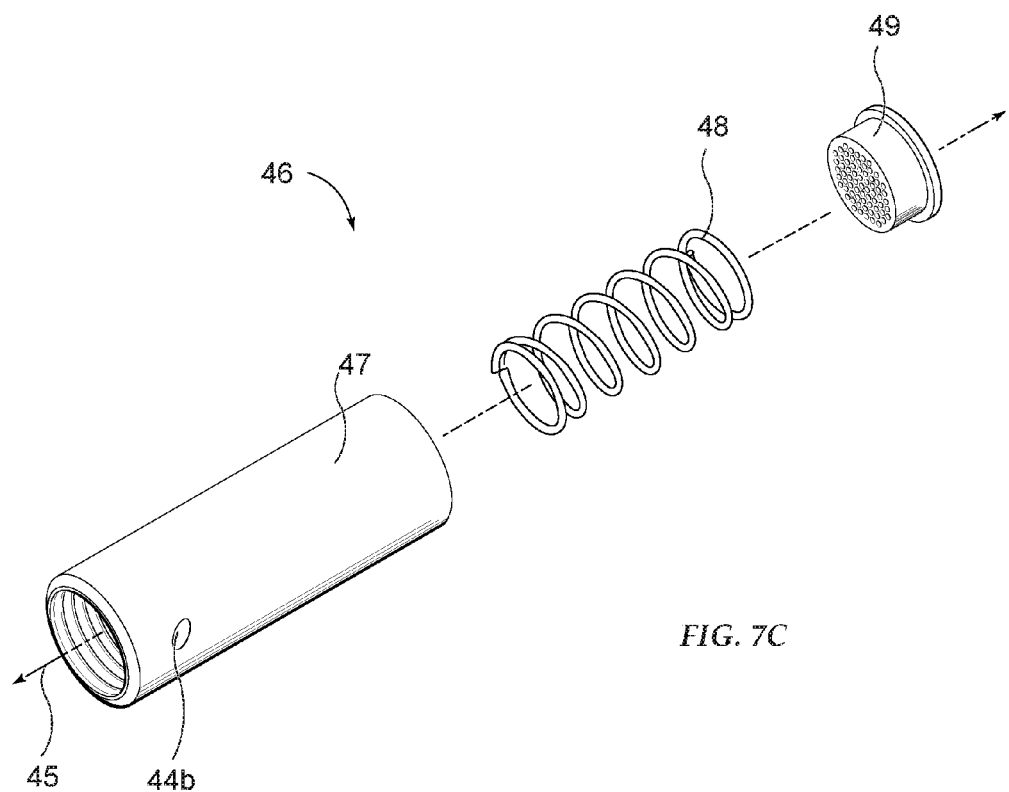
FIG. 7C is an enlarged exploded view thereof.

Regarding FIG. 7B, an exploded view and enlarged view FIG. 7C is provided to illustrate components in the flower cartridge 46 not present in the liquid cartridge 41 embodiment. In this particular interchangeable embodiment, a mesh container 49 is provided for holding flower or leaf material, that could be smoked; but instead a user desires to dry out with heat and smoke the fumes or vapor created therefrom. A wire coil 48 is provides to transfer heat from the heating element to the mesh container. This wire coil 48 is needed to dissipate heat generated by the heating element 43 to a lower temperature more suited to flower material. As stated herein, an air intake port 44b is configured on a side wall 47 of the flower cartridge 46 for intruding air in the smoking device inhale function. The intake air port 44b is not located on the cooker chamber 40 side wall as to not provide a means for exhaled air escape.

Also with regard to FIG. 7C, it should be appreciated that axis 45 defines clear and definite subject matter in an elongated electronic cigarette in that all components 20, 40, 70, 80, 90 are arranged about an elongated axis.

Figure 7D:
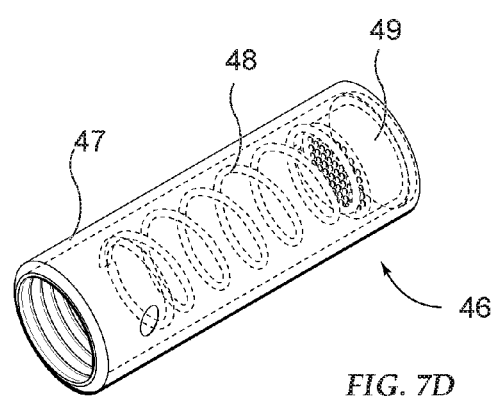
FIG. 7D is an isometric view of the accessory for vaporizing leaf material with broken lines revealing internal components.

Regarding FIG. 7D the flower cartridge 46 is further illustrated with internal components as dashed lines. Importantly, the flower chamber housing 47 has threads on both ends connecting to the igniter 71 having threads disposed around the heat element 43, and further connecting to threads provided in the diverter valve 91 assembly 90.

Figure 7E:
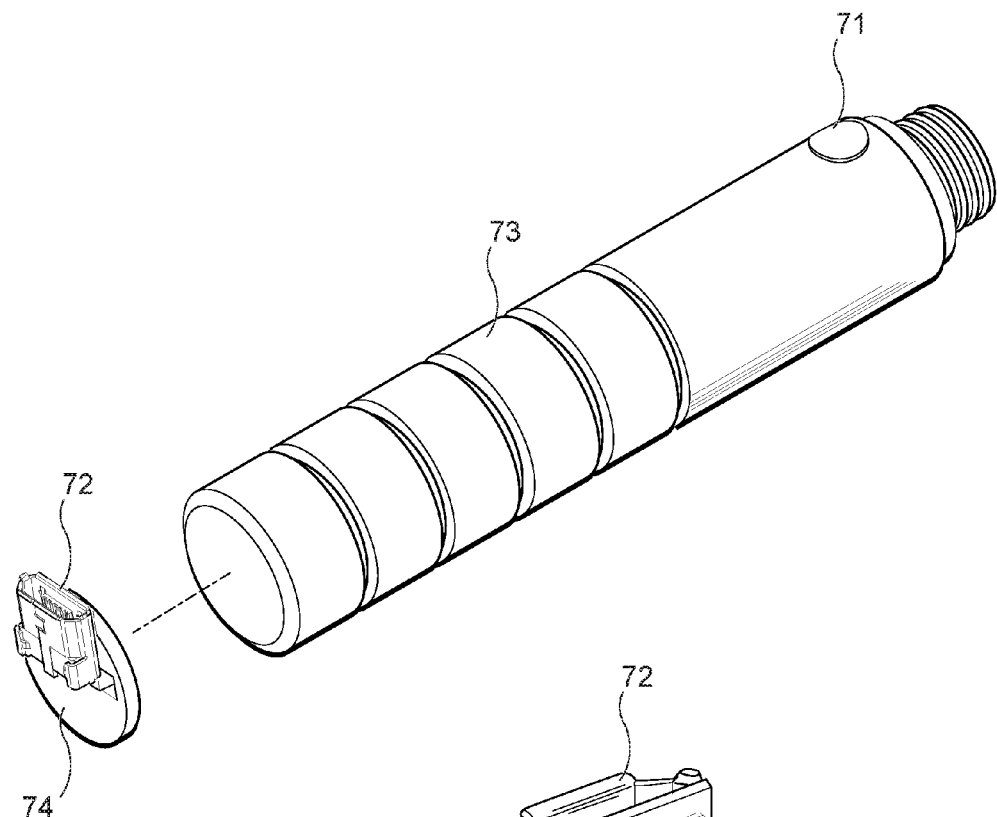
FIG. 7E and FIG. 7F are enlarged views of components illustrated in FIG. 7A.
Figure 7F:
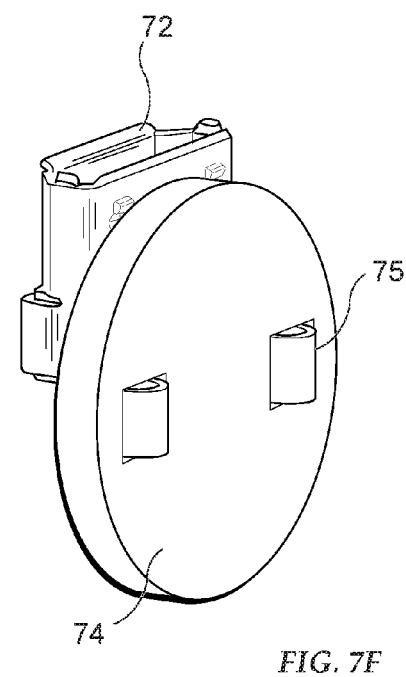

FIG. 7E and FIG. 7F shows views of igniter 71 (with igniter button) configured to rechargeable batteries 73, which are in turn coupled to a printed circuit board (PCB) 74 via electrical contacts 75. A mini or micro USB port is further provided coupled to the charging port for providing power to recharge batteries via a charging circuit provided to the PCB. In a preferred embodiment, the PCB further has a voltage regulator that together with the heating element 43 provides a proper temperature to liquid cartridge 41 (or flower cartridge 46).

Figure 8A:
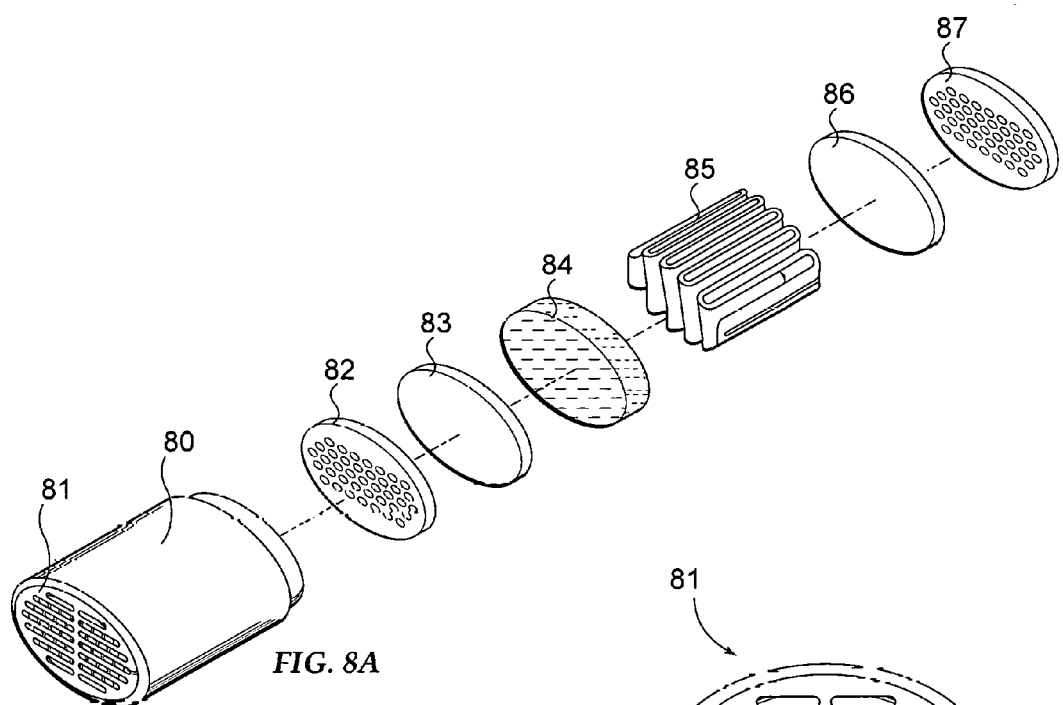
FIG. 8A is an exploded view of a filter assembly of the present invention.
Figure 8C:
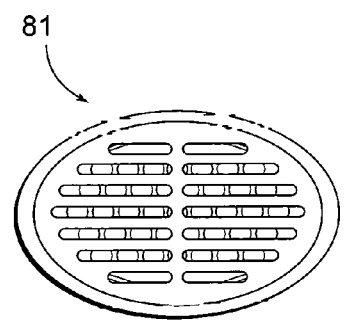
FIG. 8C is an end view thereof.
Figure 8B:
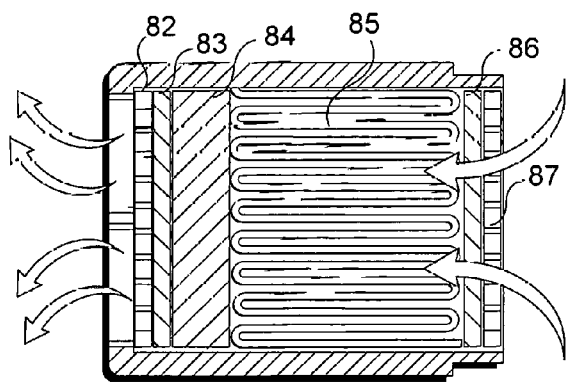
FIG. 8B is a cross-sectional view thereof taken along line 8B-8B in FIG. 1.

With regard to FIG. 8A, an exploded view of the filter assembly 80 of the present invention is provided showing components 82, 83, 84, 85, 86, 87 normally housed therein. FIG. 8B is a cross-sectional view thereof taken along line 8B-8B in FIG. 1. As shown, the filter assembly 80 has a fibrous corrugated paper filter 85 flanked by a charcoal granules 84 filter and a first felt filter 86. A second felt filter 83 is provided adjacent to the charcoal granules 84 and this unit 83, 84, 85, 86, is flanked by first 82 and second 87 screen filters. Stated differently, the first screen filter 82 is adjacent to the first 83 of the pair of felt filters 83, 86; and the second screen filter 87 is adjacent to the second 86 of the pair of felt filter 83, 86. FIG. 8C is an end view illustrating filter assembly 80 having an additional grated end piece 81 where ultimately exhaled air is filter discharged as shown with arrows in FIG. 6 and FIG. 8B.

Figure 9A:
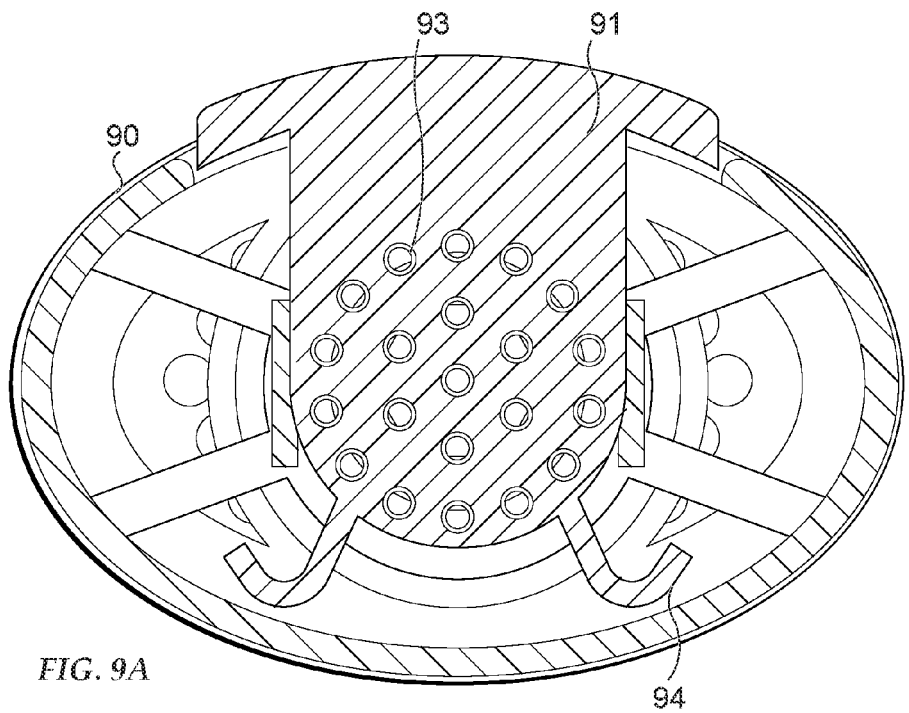
FIG. 9A is a cross-section view of the diverter valve assembly taken along line 9A-9A in FIG. 3.
Figure 9B:
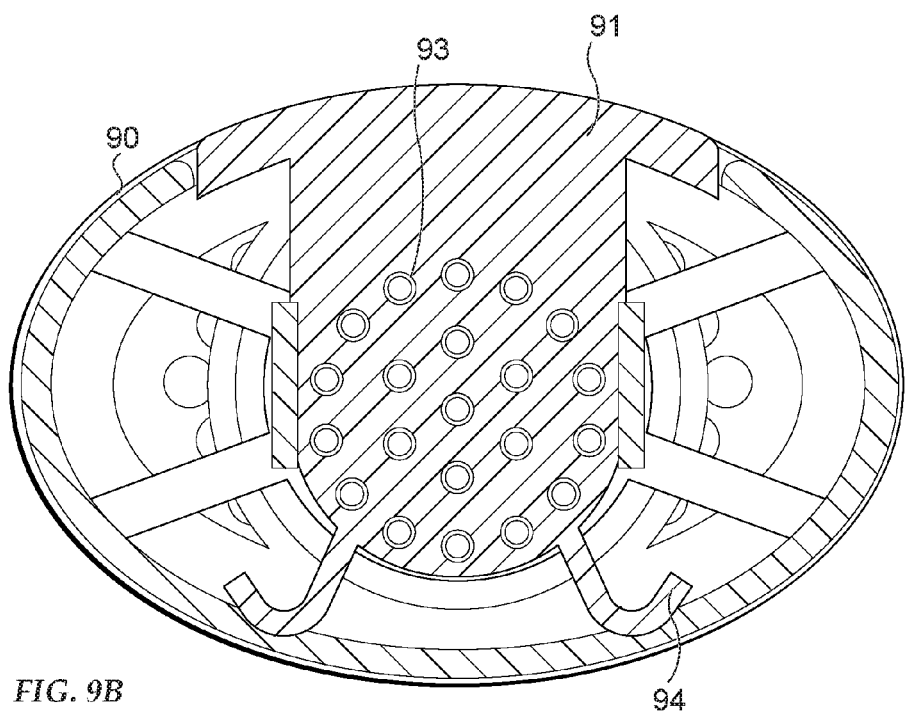
FIG. 9B is a cross-sectional view of the diverter valve in the depressed position illustrating operation thereof.

As stated and now turning to FIG. 9A, a diverter valve 91 assembly 90 is provided for blocking air flow through the cooker chamber 40 and thereby allowing air forced into the mouth piece 20 to be diverted around the cooker chamber 40. The exhaled air is then travels between the batteries 73 and the battery portion 71 housing as shown particularly in FIG. 6. In the relaxed, unpressed state, the diverter valve aligns with a fixed disk 92 so that the apertures on the diverter valve 91 and the fixed disk 92 allow air to pass therethrough. This is the inhale function. The exhale filter function herein is provided by FIG. 9B wherein when the diverter valve button 91 is depressed, the apertures are misaligned (askew) and force air around the outer portion of valve body 40, 70. A pair of curved arms 94 are provided at an opposite end with respect to the button 91 wherein the pair of arms 94 are configured to deform slightly when the diverter valve button 91 is pressed. Hence when the button 91 is released the arms return to the undeformed state.

Figure 10:
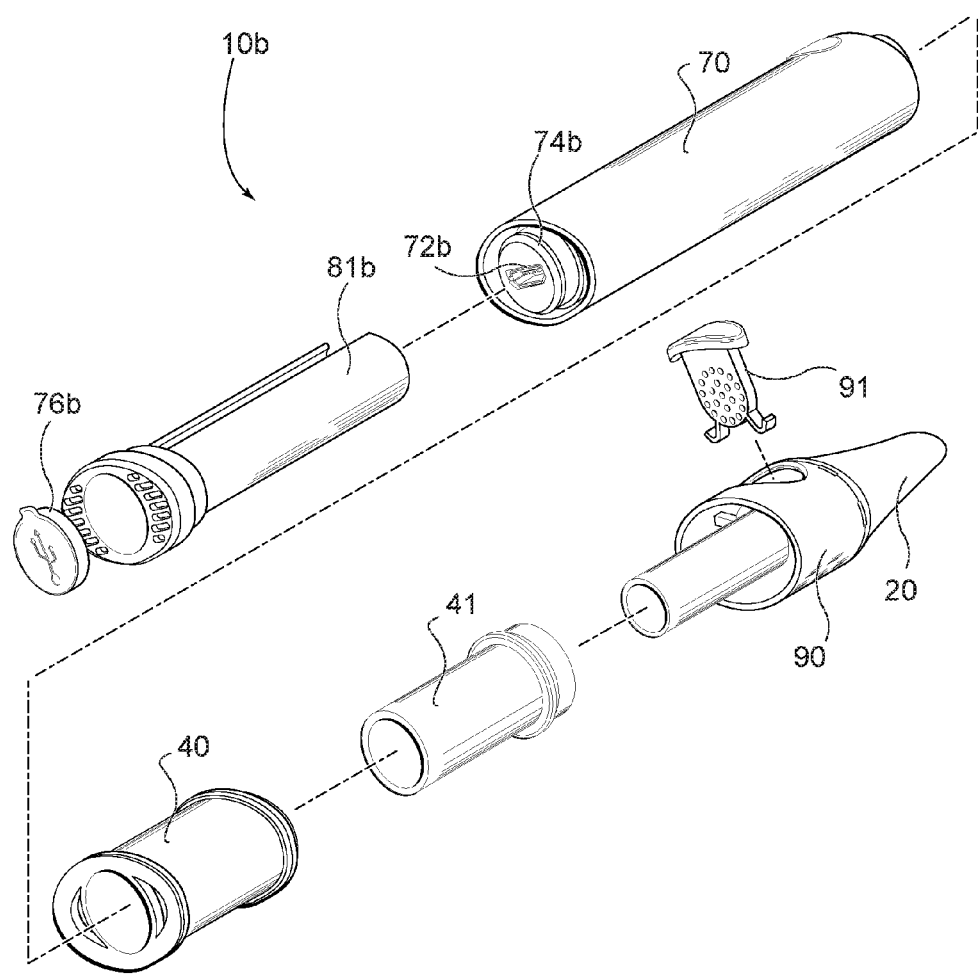
FIG. 10 is an exploded view of a second embodiment having a hollow cylindrical filter.

FIG. 10 illustrates an exploded view of a second embodiment 10b having a hollow cylindrical filter 81b. In this example, the PCB 74b has a mini USB port 72b configured axially and the cylindrical filter 81b is able to filter air around an outer portion thereof with components such as batteries 73 configured inside the hollowed out portion 81b. An end cap 76b is optionally provided covering the USB 72b.

While the particular Hybrid E-Cigarette/Vaporizer with Exhale Filter Capability herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

What is claimed is:

1. An electronic cigarette comprising:
   a mouth piece configured to a cooker chamber containing heated material;
   a body portion coupled to the cooker chamber wherein an electric heating element is provided to heat said heated material;
   a battery configured inside the body portion providing current to the electric heating element; and
   a diverter valve assembly for blocking air flow through the cooker chamber and thereby allow exhaled air forced into the mouth piece to be diverted around the cooker chamber, further wherein the diverter valve assembly further comprising:
      a diverter valve having a button for depressing with a finger or a thumb at one end; and
      a fixed disk configured as an abutment to the diverter valve, the fixed disk and the diverter valve each having a plurality of apertures where said plurality of apertures are aligned when the diverter valve is in the open positon and wherein the plurality of apertures are askew when the diverter valve is in the closed position.

2. The electronic cigarette of claim 1, the diverter valve further comprising a pair of curved arms at an opposite end with respect to the button wherein the pair of arms are configured to deform slightly when the button is depressed and when the diverter valve is in the closed position and wherein when the button is released the arms return to an undeformed state.

3. The electronic cigarette of claim 1, further comprising:
   a printed circuit board (PCB) coupled to the battery, the battery being a rechargeable battery;
   a charging circuit configured to the PCB; and
   a micro universal serial bus (USB) port for connecting to a power source for recharging the battery.

4. The electronic cigarette of claim 3 further comprising a PCB cover configured adjacent to the PCB further wherein the micro USB port is accessible through an aperture in a side wall in the body portion.

5. The electronic cigarette of claim 1, further comprising a filter assembly coupled to the body portion at a distal end thereof, the filter assembly further comprising:
   a corrugated paper filter; and
   a pair of felt filters configured on opposite sides of the corrugated paper filter.

6. The electronic cigarette of claim 1 wherein the body portion has an outer portion comprising aluminum wherein the cooker chamber has an outer wall comprising glass and wherein the mouth piece comprises thermoplastic material, the thermoplastic material further comprising flavored material.

7. The electronic cigarette of claim 1 further comprising a button electrically configured to the battery and the heating element, the button for starting said heating element.

8. The electronic cigarette of claim 1 the cooker chamber further comprising a removable liquid cartridge, the removable liquid cartridge having a cylindrical liquid chamber therewithin for containing the liquid.

9. A vapor smoking device comprising:
   a mouth piece configured to a cooker chamber containing heated material;
   a body device coupled to a the cooker chamber wherein an electric heating element is provided to heat said heated material;
   a battery configured inside the body portion providing current to the electric heating element; and
   a filter assembly coupled to the body portion at a distal end thereof, wherein the filter assembly further comprising:
      a corrugated paper filter; and
      a pair of felt filters configured on opposite sides of the corrugated paper filter.

10. The vapor smoking device of claim 9, the filter assembly further comprising:
    a charcoal granules filter adjacent to the corrugated paper filter and adjacent to a first of the pair of felt filters; and
    a first and a second screen filter, the first screen filter adjacent to the first of the pair of felt filters, the second screen filter adjacent to a second of the pair of felt filters.

11. The vapor smoking device of claim 9 further comprising:
    a button electrically configured to the battery and the heating element, the button for starting said heating element; and
    a removable liquid cartridge configured within the cooker chamber, the igniter having threads at an end thereof, the removable liquid cartridge further having complementary threads to connect to the igniter.

12. A vapor smoking device comprising:
    a cooker chamber;
    a mouth piece configured to a cooker chamber containing heated material;
    a body portion coupled to a the cooker chamber wherein an electric heating element is provided to heat said heated material;
    a removable cartridge configured within the cooker chamber for holding the heated material to be vaporized;
    a battery configured inside the body portion providing current to the electric heating element, wherein the body portion has an outer portion comprising aluminum wherein the cooker chamber has an outer wall comprising glass and wherein the mouth piece comprises thermoplastic material; and
    a diverter valve assembly for blocking air flow through the cooker chamber and thereby allow exhaled air forced into the mouth piece to be diverted around the cooker chamber.

13. The vapor smoking device of claim 12, wherein the removable cartridge comprises a removable flower cartridge, the removable flower cartridge further comprising:
    a mesh container for holding said flower material;
    a wire coil to transfer heat from the heating element to the mesh container, the wire coil for the purposes of dissipating heat generated by the heating element to a temperature optimum for the flower material; and
    an air intake port on a side wall of the flower cartridge for introducing air in a smoking device inhale function.

* * * * *